United States Patent
Lynes et al.

(10) Patent No.: US 11,693,882 B2
(45) Date of Patent: Jul. 4, 2023

(54) SYSTEM AND METHOD FOR OFFLINE CAPABILITY FOR MOBILE DEVICES INCLUDING ASYNCHRONOUS THREADS

(71) Applicant: ORACLE INTERNATIONAL CORPORATION, Redwood Shores, CA (US)

(72) Inventors: Matthew Lynes, Newport Beach, CA (US); Victor Matskiv, Walnut Creek, CA (US); Jayant Thomas, San Ramon, CA (US)

(73) Assignee: Oracle International Corporation, Redwood Shores, CA (US)

( * ) Notice: Subject to any disclaimer, the term of this patent is extended or adjusted under 35 U.S.C. 154(b) by 574 days.

(21) Appl. No.: 16/810,066

(22) Filed: Mar. 5, 2020

(65) Prior Publication Data
US 2020/0202991 A1    Jun. 25, 2020

Related U.S. Application Data

(62) Division of application No. 13/827,073, filed on Mar. 14, 2013, now abandoned.
(Continued)

(51) Int. Cl.
*G06F 16/00*    (2019.01)
*G06F 16/27*    (2019.01)
(Continued)

(52) U.S. Cl.
CPC ........... *G06F 16/273* (2019.01); *G16H 10/20* (2018.01); *G16H 15/00* (2018.01)

(58) Field of Classification Search
CPC .................................................. G06F 16/273
See application file for complete search history.

(56) References Cited

U.S. PATENT DOCUMENTS

| 6,480,847 B1 | 11/2002 | Linenbach |
| 2005/0070259 A1 | 3/2005 | Kloba et al. |
(Continued)

FOREIGN PATENT DOCUMENTS

| JP | H04299758 A | 10/1992 |
| JP | H11134277 A | 5/1999 |
(Continued)

OTHER PUBLICATIONS

Patent Cooperation Treaty (PCT) International Search Report and Written Opinion in PCT International Appl. No. PCT/US13/41096 (International Filing Date of May 15, 2013), dated Mar. 13, 2014 (11 pages).

(Continued)

*Primary Examiner* — Chelcie L Daye
(74) *Attorney, Agent, or Firm* — Kraguljac Law Group, LLC

(57) ABSTRACT

Systems and methods are described herein that provide a system associated with a CRA application framework with offline capability for mobile devices. In one example embodiment, a network request is received via network communications from a mobile device. The request is identified and multiple processing threads are initiated that separate operations for performing the request. A Self Describing Object (SDO) is generated and is returned in response to a fetch request. This allows the mobile device to input data while offline from a server and to minimize network interactions therebetween.

15 Claims, 5 Drawing Sheets

Related U.S. Application Data

(60) Provisional application No. 61/662,050, filed on Jun. 20, 2012.

(51) Int. Cl.
*G16H 10/20* (2018.01)
*G16H 15/00* (2018.01)

(56) References Cited

U.S. PATENT DOCUMENTS

| | | |
|---|---|---|
| 2008/0256128 A1 | 10/2008 | Pierce et al. |
| 2008/0288275 A1 | 11/2008 | Houriet et al. |
| 2009/0248693 A1 | 10/2009 | Sagar et al. |
| 2012/0101837 A1 | 4/2012 | McCorkle et al. |

FOREIGN PATENT DOCUMENTS

| | | |
|---|---|---|
| JP | 2003196391 A | 7/2003 |
| JP | 2003280931 A | 10/2003 |
| JP | 2005528706 A | 9/2005 |
| JP | 2010050742 A | 3/2010 |

OTHER PUBLICATIONS

Gaggioli, et al., "A Mobile Data Collection Platform for Mental Health Research." Personal and Ubiquitous Computing 17.2 (2013): 241-251.

Johnson et al., "An Electronic Health Record Based on Structured Narrative" Journal of the American Medical Informatics Association vol. 15 No. 1 Jan./Feb. 2008, Retrieved online from: http://171.67.114.118/content/15/1/54.full.pdf+html>.

IN Examination Report dated Sep. 27, 2019 for IN application No. 17386/CHENP/2014 filed Oct. 7, 2014. (pp. 1-8).

Office Action dated Sep. 5, 2017 for Chinese Patent Application No. 201380030137.5.

SYSTEM AND METHOD FOR OFFLINE CAPABILITY FOR MOBILE DEVICES INCLUDING ASYNCHRONOUS THREADS

CROSS REFERENCE TO RELATED APPLICATIONS

This disclosure is a Divisional Application of U.S. application Ser. No. 13/827,073 filed Mar. 14, 2013, and claims the benefit of U.S. provisional patent application Ser. No. 61/662,050 filed Jun. 20, 2012, which are both incorporated by reference in their entirety.

BACKGROUND

In network communications from a mobile device, network applications attempt to provide a smooth and consistent mobile user experience whether the device is connected to network, disconnected from the network, or the connection is intermittent. Mobile computing devices use specialized applications to perform communications with remote servers. Application developers need to code using object oriented programming language such as Objective C to implement functions of the communications. This controls how and when functions (e.g., caching, encryption, etc.) are performed during communications. This has been a restriction in prior techniques due to the specific coding needed. As such, requesting data that needs to be generated from a remote server poses network communication issues.

For example, clinical trials are sets of tests in medical research and drug development that generate safety and efficacy data, such as information about adverse drug reactions and adverse effects of treatments for health interventions (e.g., drugs, diagnostics, devices, therapy protocols). Furthermore, information about the design of the clinical study, such as information about drugs, diagnostics, devices and protocols may also be included.

A trip report stores information regarding a clinical study. Therefore, trip reports are highly customizable and include significant data. It is desirable to edit and display the trip report on a mobile device without having to customize the interface with the mobile device or having to repeatedly access the remote server. Likewise, it is difficult to standardize trip reports due to the interaction of the business components and the trip report web service.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Systems and methods are described herein that provide a mobile clinical research associate (CRA) application framework that is built to support offline capabilities. The CRA application framework provides a generic way to encrypt and cache data using declarative tags to databases and file systems on a mobile device. Using declarative programming minimizes the amount of coding required to enable the CRA application framework. The CRA application framework allows users to cache offline data, enables downloading of data to a mobile device, and operate the mobile device while offline.

In one embodiment, the CRA application framework performs trip report related activities. Creating a trip report is one of the most resource intensive operations. Typically, a server processing the request to create a trip report would also generate the trip report together sequentially in the same process. To reduce the amount of strain put on the CRA application framework, the activities related to the trip report are identified and performed asynchronously. Accordingly, the application framework improves processing efficiency by generating and initiating different threads to asynchronously process the request to create the trip report and to generate the trip report. By separating the resource intensive operations into separate threads, the CRA application framework achieves better control over the server resources, allows for greater scalability, and makes the system more reliable.

Figure 1:
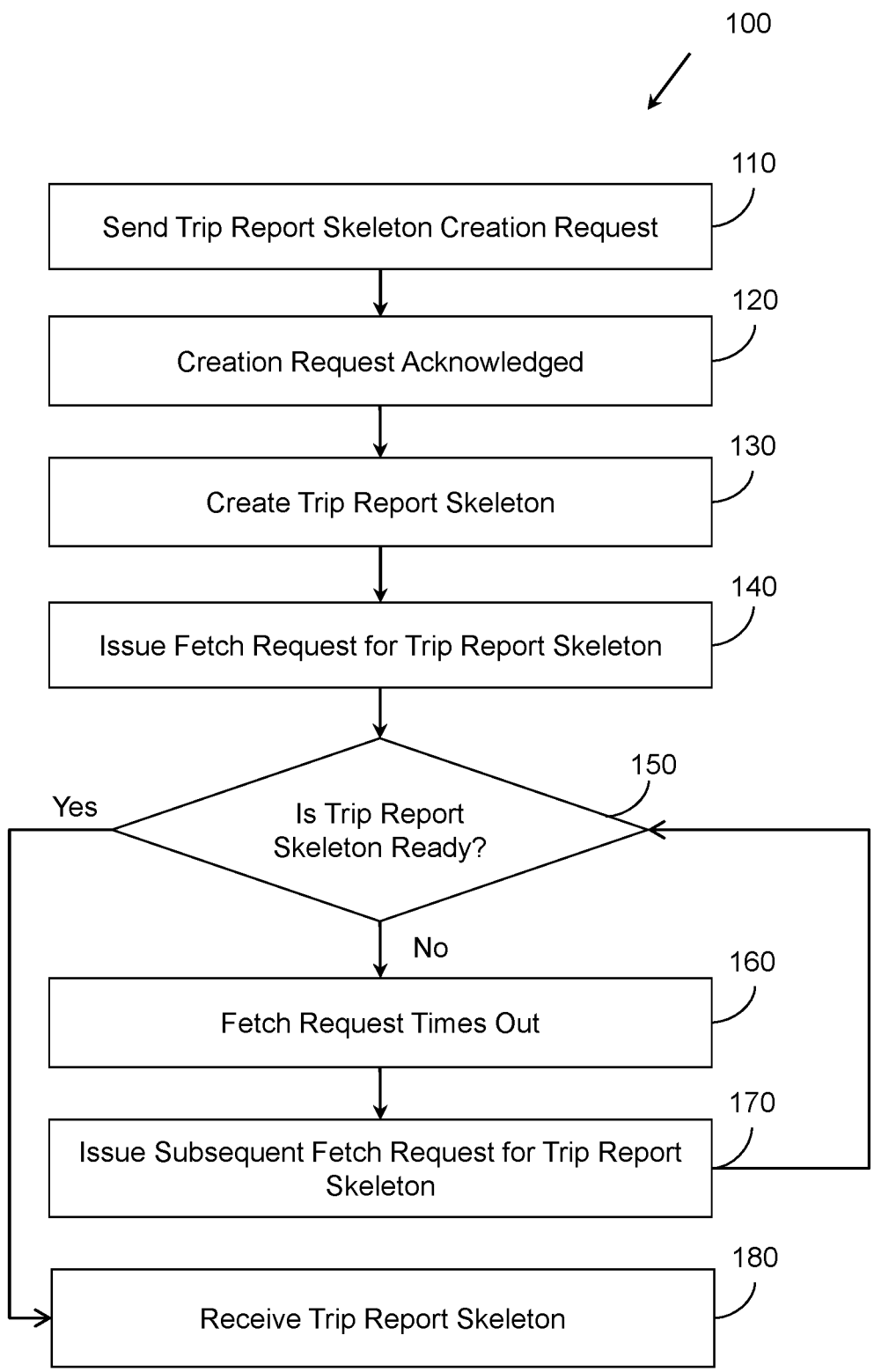
FIG. 1 illustrates one embodiment of a method associated with a clinical research associate (CRA) framework for offline capability.

For example, FIG. 1 illustrates an example embodiment of a method associated with a CRA application framework with offline capability. The method 100 is performed in a CRA application framework used for managing data from clinical studies. The CRA application framework facilitates communication between mobile devices and a server.

A user visiting a clinical setting has a mobile device that is used to store and manage data about their trip to the clinic. To ensure the desired data is acquired, the mobile device includes a user interface for entering trip report data into predefined spaces in a trip report skeleton. The trip report skeleton is first requested from the server via network communications. To receive a trip report skeleton, a creation request to create a trip report skeleton is sent from the mobile device to a server. The server identifies the request as being for a trip report skeleton and in response, controls the processor to initiate multiple separate threads for asynchronous processing of the request. The server assigns and processes the request in a first thread at 110 in a processor of the server. At 120, the creation request is acknowledged by the server by transmitting an electronic acknowledgment to the mobile device. At 130, a task for generating/creating the trip report skeleton is assigned to and executed in a second thread on the server. To better distribute server resources, the first thread is operated asynchronously from the second thread.

At 140, the mobile device issues a fetch request to retrieve the created trip report skeleton. Because the first thread and the second thread operate asynchronously, the trip report skeleton may not be ready when the trip report skeleton is requested. At 150, a determination is made whether the trip report skeleton is ready to be sent to the mobile device by at least accessing and checking a memory containing the trip report skeleton. If the trip report skeleton is not ready, the method 100 proceeds to 160 where the system triggers a signal to cause the fetch request to time out so the system no longer waits and cancels the fetch request. At 170, the mobile device issues a subsequent fetch request to retrieve the trip report skeleton. The timing of sending additional fetch requests may comply with a predetermined schedule. Alternatively additional fetch requests may be sent as soon as the fetch request times out (are canceled/disregarded) at 160 or after a predetermined amount of time elapses after the fetch request times out at 160. The method 100 then returns to step 150 to determine whether the trip report is ready to be sent to the mobile device.

If the trip report skeleton is ready, the method 100 proceeds to step 180 where the trip report skeleton is received by the mobile device. At 180, the mobile device receives the trip report skeleton as a Self Describing Object (SDO). Regardless of the customization of the clinical study, the clinical data can be entered into the SDO on the mobile device. The SDO contains metadata that enables the mobile device to render the trip report skeleton on the mobile device. Therefore, the mobile device does not need to access a remote server when data is being entered into the trip report skeleton. This reduces the number of times that the mobile device has to access the remote server.

Figure 2:
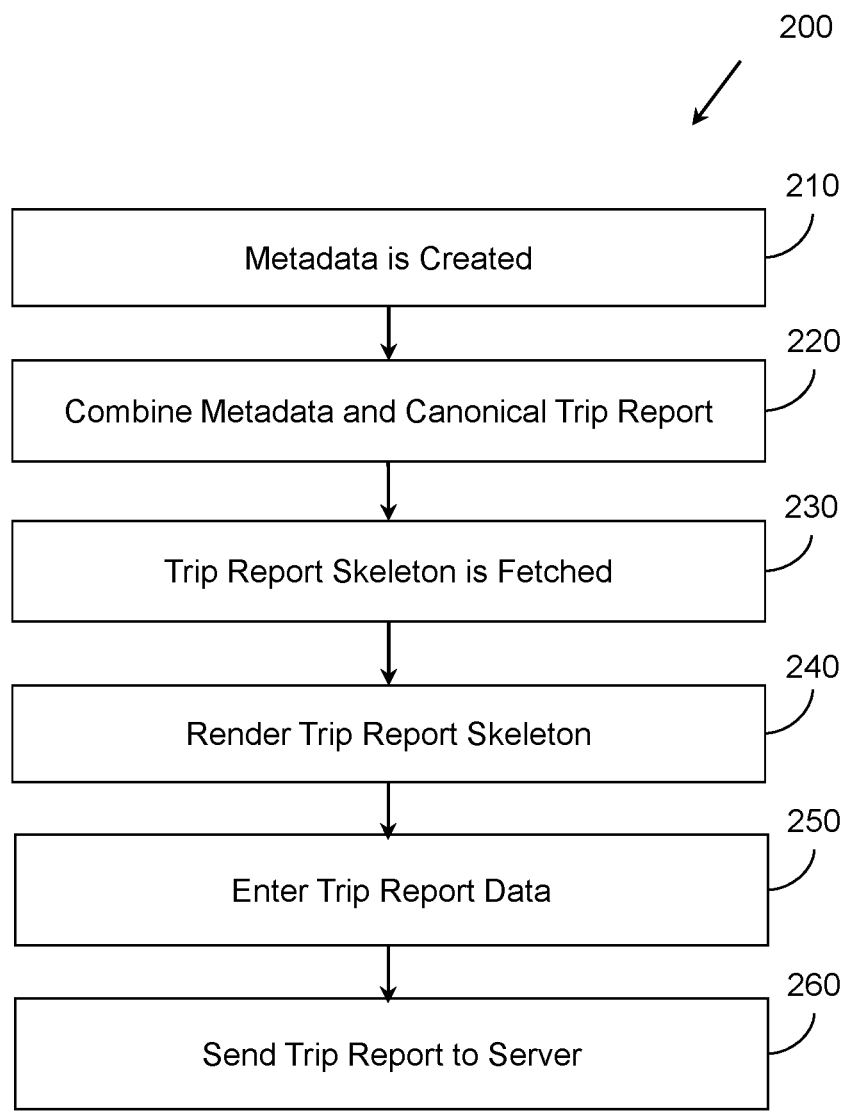
FIG. 2 illustrates another embodiment of a method associated with a CRA framework for offline capability.

FIG. 2 illustrates an embodiment of a method associated with a CRA application framework with offline capability. The trip report skeleton is generated as a Self Describing Object (SDO). One advantage of the trip report skeleton being in an SDO format is that generic tools can be used to manipulate trip report data. Self-describing data contains the information that tools need to manipulate various types of data correctly. Another advantage of the trip report skeleton being in an SDO format is that it makes the CRA application framework more robust and flexible. Multiple programs running on different devices (e.g., mobile device, server) may interface to a single program despite differences in where the different devices place trip report data.

At 210, metadata is created for rendering a trip report on a mobile device and stored on a server. At 220, the stored metadata is combined with a canonical trip report to create a skeleton trip report in an SDO format. At 230, the skeleton trip report is fetched by the mobile device. At 240, the mobile device renders the skeleton trip report based on the embedded metadata. At 250, trip report data is entered in the skeleton trip report. Because the trip report skeleton is maintained on the mobile device as an SDO, data is entered by the mobile device into the skeleton trip report regardless of whether the server has immediate access to the data. Data can be entered when the mobile device is offline (i.e., disconnected from the server).

In response to the mobile device meeting mobile device parameters, at 260 the completed trip report is sent back to the server to be stored. The device parameters may include completing the trip report skeleton with a predetermined percentage of trip report data. Alternatively the device parameters may be a function of the relationship between the mobile device and the server. For example, the completed trip report may be sent to the logic when a network link is established between the mobile device and the server.

Figure 3:
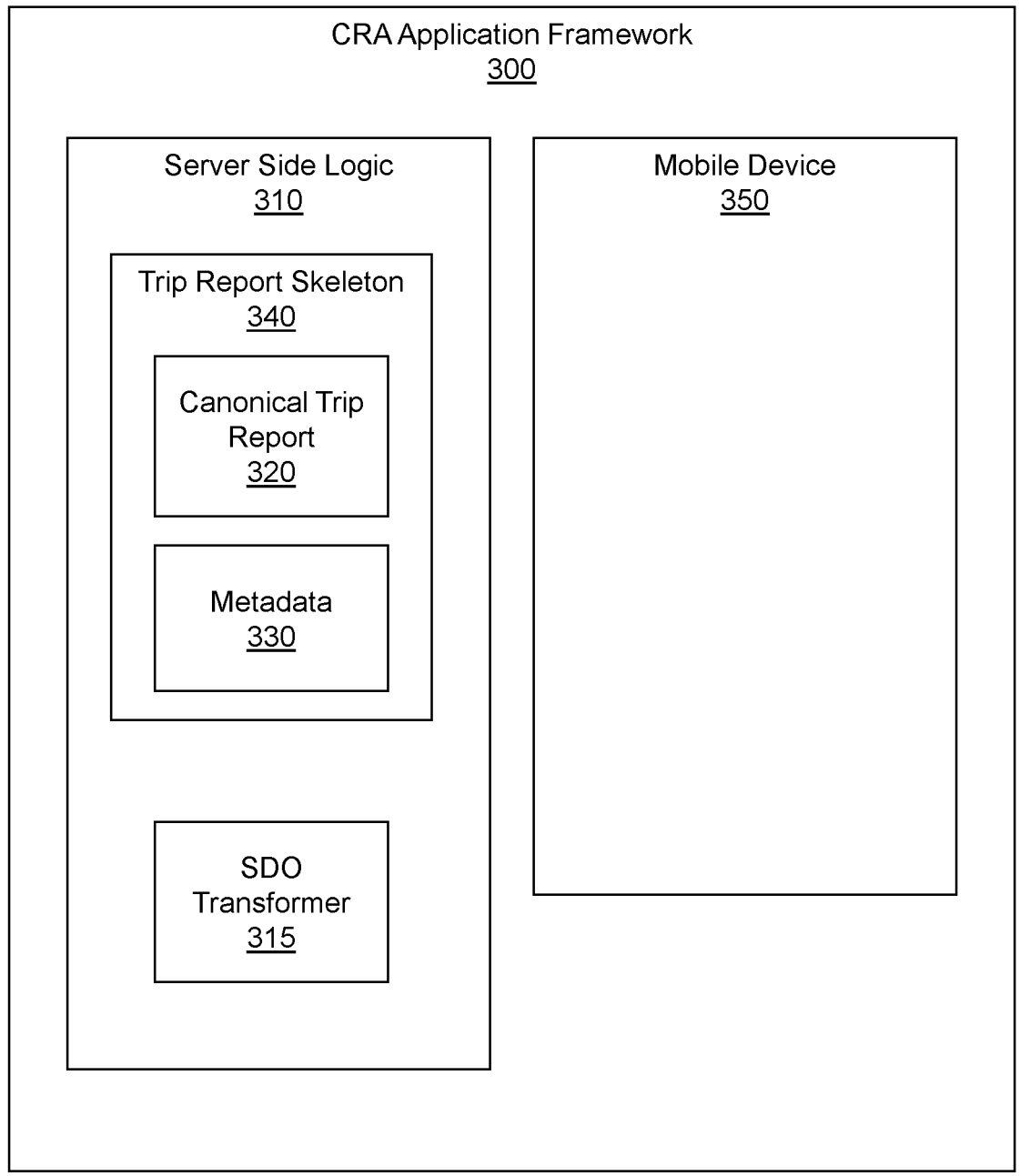
FIG. 3 illustrates another embodiment of a system associated with a CRA framework for offline capability.

FIG. 3 illustrates one example embodiment of a system associated with a CRA application framework with offline capability. Trip reports are heavily customized. Customizing the trip report changes the underlying data structure, related clinical components, and the trip report web service that facilitates communication between a server side logic 310 and a mobile device 350. The server side logic 310 and the mobile device 350 communicate trip report data using a CRA application framework 300.

The server side logic 310 stores a canonical trip report 320 and metadata 330. The canonical trip report 320 is a generalized structure that is linked to a custom trip report. Therefore, a custom trip report may be highly customized making the custom trip report form inappropriate for distribution to multiple users. The canonical trip report 320 is generalized so that the canonical trip report 320 can be distributed to a number of users for a number of trips even when the users are employing different mobile devices.

The metadata 330 is used to render (e.g., individual screen rendering, individual field rendering and validation, screen transitions, and handling data change events) the canonical trip report 320 on the mobile device 350. For example, the canonical trip report 320 supports custom activity attributes (e.g., checklist functionality). The metadata 330 renders the custom activity attributes on the mobile device 350. The metadata 330 is generated and stored on the server side logic 310 by an administrator. Once the metadata is stored, any number of mobile devices, like the mobile device 350 can use the metadata for rendering. The creation request sent by a mobile device may include device data such as a mobile device identifier so that the correct metadata for a mobile device is known.

The canonical trip report 320 and the metadata 330 are combined by an SDO transformer 315 on the server side logic 310 in a memory to create a trip report skeleton 340. The trip report skeleton 340 is a Self Describing Object (SDO). SDOs, like the canonical trip report 320, are defined in an object oriented computer programming language (e.g., JAVA). For example, from the perspective of the server side logic, the trip report skeleton 340 is an SDO that is a plain Java object, structured in a JavaScript Object Notation (JSON) for Java to JSON deserialization. The canonical trip report 320 uses classes that contain special annotations to facilitate use of XML serialization.

Accordingly, SDO classes are structurally similar to canonical trip report classes. The difference between the canonical trip report 320 and the trip report skeleton 340 is that the trip report skeleton 340 is in an SDO format and additionally contains metadata 330. The server side logic 310 also provides application programming interfaces (APIs) for the mobile device 350 to load and synchronize the trip report skeleton 340.

The SDO transformer 315 also reverses the conversion from trip report skeleton 340 back to a canonical trip report 320. Some of the features of a custom trip report may be lost when the custom trip report is converted to a canonical trip report 320. Accordingly the conversion of the custom trip report to the canonical trip report 320 is considered "lossy." However, information lost during the conversion from the custom trip report to the canonical trip report 320 is restored during the reverse conversion. For example, the server side logic 310 persists the custom trip report by saving the custom trip report. When the server side logic receives a trip report skeleton 340 with information about a trip, the resulting modified trip report skeleton is merged with the custom trip report during the reverse conversion. Accordingly, the trip report data lost by using a trip report skeleton can be restored.

Figure 4:
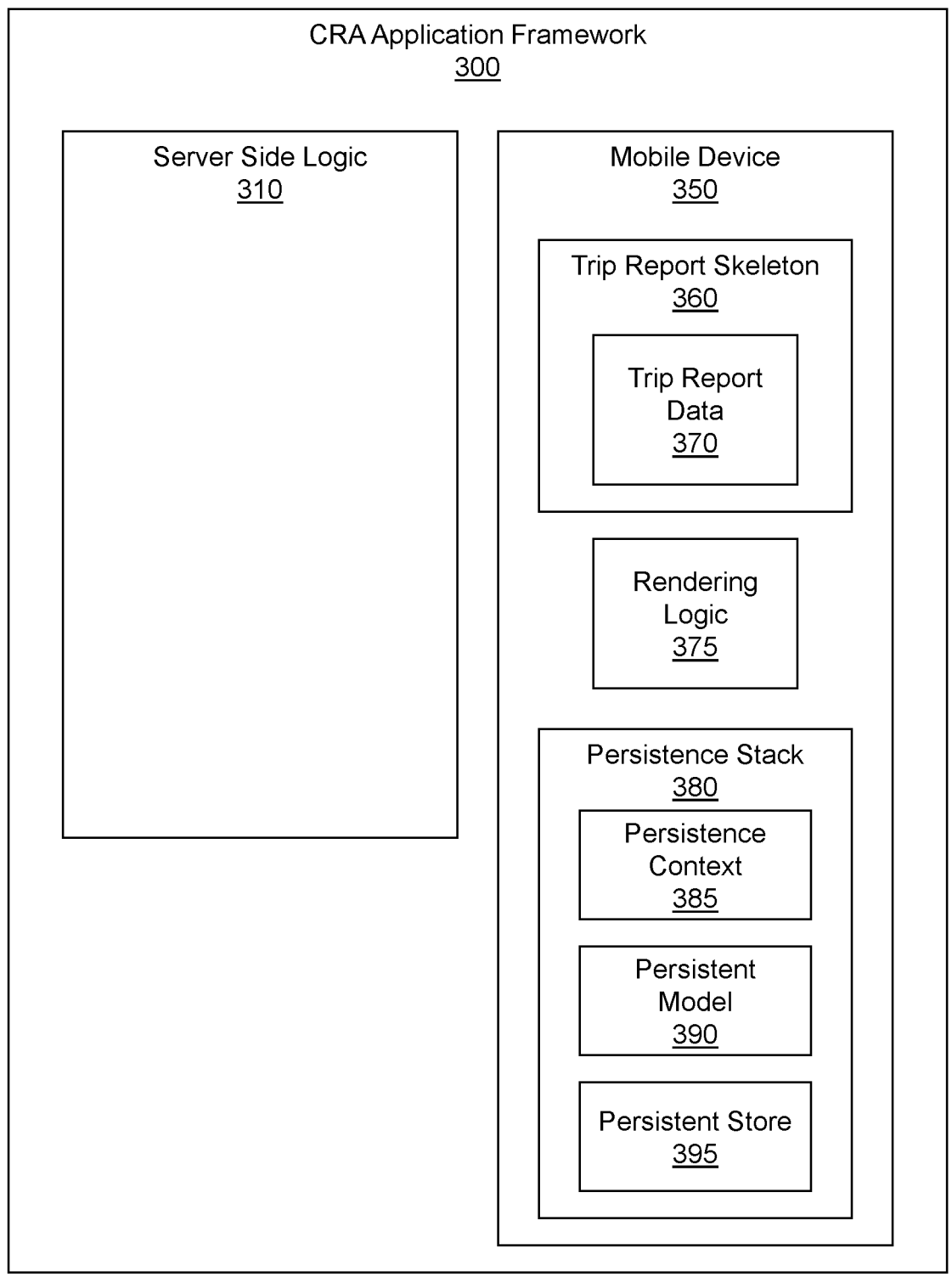
FIG. 4 illustrates another embodiment of a system associated with a CRA framework for offline capability.

FIG. 4 illustrates another example embodiment of a system associated with a CRA application framework with offline capability. The mobile device 350 has received the trip report skeleton 360 from the server via network communications. The mobile device 350 may receive the trip report skeleton 360 in the manner described with respect to FIG. 1. The mobile device 350 inputs the trip report data 370 and stores the trip report data 370 locally in the trip report skeleton 360 on the mobile device 350 of the CRA application framework system 300.

From the perspective of the mobile device 350 the trip report skeleton 360 is an SDO that is deserialised into a generic recursive dictionary/array structure. A rendering logic 375 renders the trip report skeleton 360 based on the metadata included in the trip report skeleton 360. The trip report data 370 can be manipulated regardless of whether the mobile device 350 is connected to a network, disconnected, or the connection is intermittent. When the trip report data 370 needs to be synchronized with the server side logic 310, the trip report skeleton 360 including the trip report data 370 can be sent back to the server side logic 310. Therefore, the network interactions are minimized because the trip report data 370 can be manipulated on the mobile device 350 and sent when it is convenient.

The trip report skeleton 360 is stored locally on the mobile device 350 using a persistence stack 380. The persistence stack 380 performs encryption of the trip report data 370 on the mobile device 350. The persistence stack 380 also stores and retrieves trip report skeletons 360, tracks changes to the trip report data 370, and performs updates.

The persistence stack 380 includes a persistent context 385, a persistent model 390, and a persistent store 395. The persistent context 385 registers objects, such as the trip report skeleton 360 which is an SDO, by associating objects with a unique key. One of ordinary skill in the art will recognize there are a number of ways to associated objects with a unique key. For example, the persistent context 385 may assign a unique key to the object using a persistent context delegate method.

The persistent context 385 also tracks changes occurring in the trip report skeleton 360 by assessing the trip report skeleton 360 to be in a dirty state when the persistence stack 380 detects that the trip report data 370 has been changed. If the trip report skeleton 360 is deemed dirty, an update action is scheduled for the trip report data 370. The update action causes the flagged trip report skeleton 360 to be saved to the persistence context 385 thereby saving the trip report data 370. If the trip report skeleton 360 is still dirty, the update is finalized resulting in the "dirty" flag being cleared.

The persistent context 385 detects changes in the trip report skeleton 360 in response to a number of events (e.g., a change being made, initialization). For example upon initialization, the persistence context 380 verifies whether any of the managed trip report skeletons 360 are in a dirty state. If a trip report skeleton, such as trip report skeleton 360, is dirty, the persistence context 380 determines that an update operation was not completed, and the persistence context 380 subsequently reschedules the update operation for the trip report skeleton.

The persistent model 390 provides in memory collection of the trip report data 370. The persistent model 390 also loads previously persisted trip report skeletons from the persistent context. The persistent model 390 will not update earlier persisted items in the dirty state or objects with a timestamp greater than the timestamp of the incoming trip report data 370. The persistent store 395 saves the trip report skeletons like the trip report skeleton 360. The persistent store 395 also encrypts and decrypts trip report data 370.

The CRA application framework 300 enables ease of caching offline data using declarative programming and enables a user to download data to the mobile device 350 and manage the data while offline. The system caches the data on the mobile device and monitors the lifecycle of the cached data and provides dynamic synchronization capabilities. In another embodiment, the system provides widgets that are configured to display the cached data in various formats using declarative programming. In one embodiment, the system enables sensitive data to be HIPPA and CFR part 11 compliant using settings.

In another embodiment, the described methods and/or their equivalents may be implemented with computer executable instructions. Thus, in one embodiment, a non-transitory computer-readable medium is configured with stored computer executable instructions that when executed by a machine (e.g., processor, computer, and so on) cause the machine (and/or associated components) to perform the method. In another embodiment, the described systems, methods and/or their equivalents may be implemented in logic.

Figure 5:
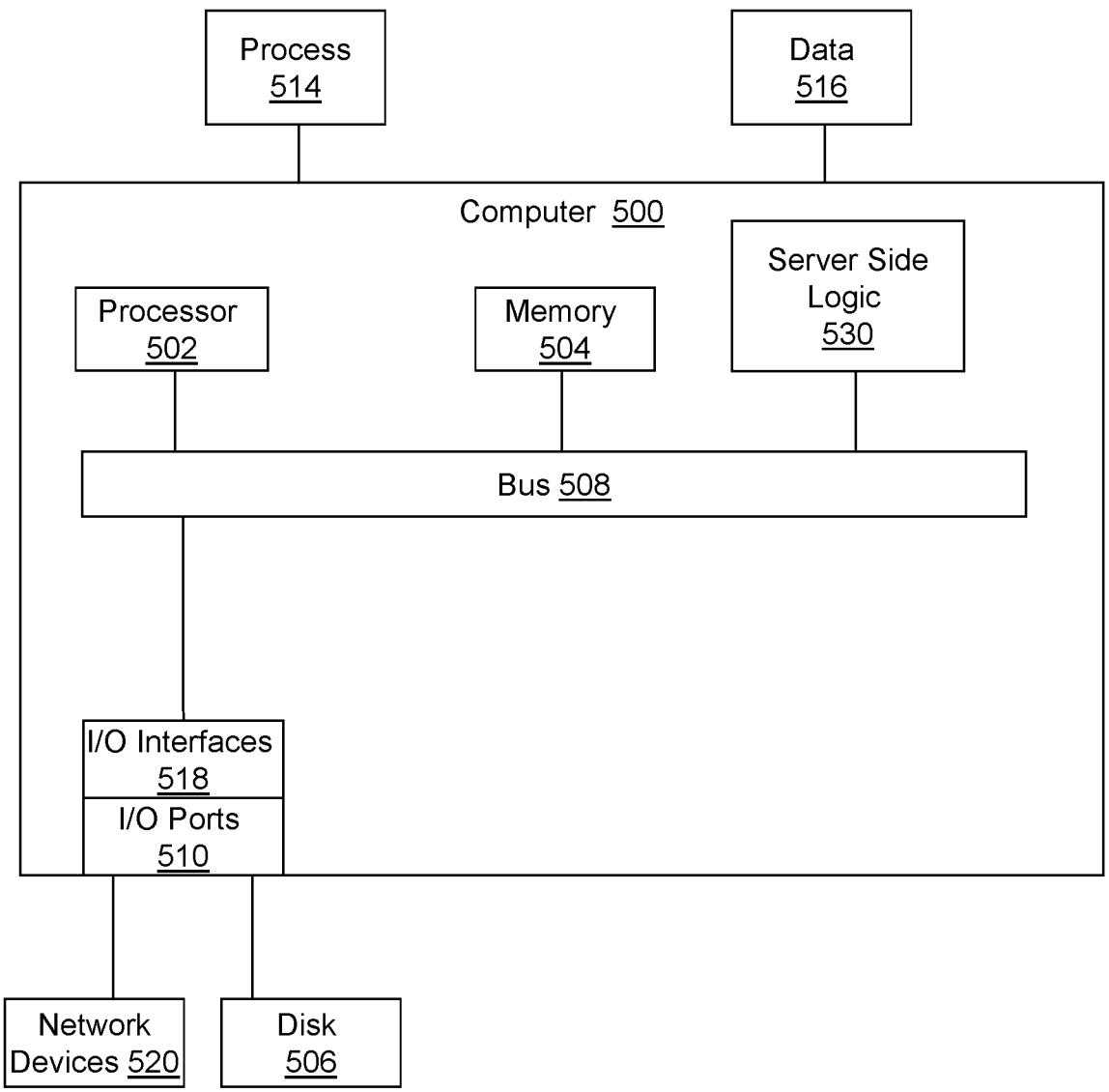
FIG. 5 illustrates an embodiment of a computing system in which example systems and methods, and equivalents, may operate.

FIG. 5 illustrates an example computing device in which example systems and methods described herein, and equivalents, may operate. The example computing device may be a computer 500 that includes a processor 502, a memory 504, and input/output ports 510 operably connected by a bus 508. In one example, the computer 500 may include a server side logic 530 configured to operate on a CRA application framework and allow a mobile device to function offline. In different examples, the server side logic 530 may be implemented in hardware, a non-transitory computer-readable medium with stored instructions, firmware, and/or combinations thereof. While the server side logic 530 is illustrated as a hardware component attached to the bus 508, it is to be appreciated that in one example, the server side logic 530 could be implemented in the processor 502.

In one embodiment, the server side logic 530 has means (e.g., hardware, non-transitory computer-readable medium, firmware) for combining a canonical trip report with metadata to create an SDO. The means may be implemented, for example, as an ASIC programmed to create the SDO. The means may also be implemented as stored computer executable instructions that are presented to computer 500 as data 516 that are temporarily stored in memory 504 and then executed by processor 502. Alternatively, the functionality of the server side logic may be implemented on a mobile device.

Generally describing an example configuration of the computer 500, the processor 502 may be a variety of various processors including dual microprocessor and other multi-processor architectures. A memory 504 may include volatile memory and/or non-volatile memory. Non-volatile memory may include, for example, ROM, PROM, and so on. Volatile memory may include, for example, RAM, SRAM, DRAM, and so on.

A disk 506 may be operably connected to the computer 500 via, for example, an input/output interface (e.g., card, device) 518 and an input/output port 510. The disk 506 may be, for example, a magnetic disk drive, a solid state disk drive, a floppy disk drive, a tape drive, a Zip drive, a flash memory card, a memory stick, and so on. Furthermore, the disk 506 may be a CD-ROM drive, a CD-R drive, a CD-RW drive, a DVD ROM, and so on. The memory 504 can store a process 514 and/or a data 516, for example. The disk 506 and/or the memory 504 can store an operating system that controls and allocates resources of the computer 500.

The bus 508 may be a single internal bus interconnect architecture and/or other bus or mesh architectures. While a single bus is illustrated, it is to be appreciated that the computer 500 may communicate with various devices, logics, and peripherals using other busses (e.g., PCIE, 1394, USB, Ethernet). The bus 508 can be types including, for example, a memory bus, a memory controller, a peripheral bus, an external bus, a crossbar switch, and/or a local bus.

The computer 500 may interact with input/output devices via the i/o interfaces 518 and the input/output ports 510. Input/output devices may be, for example, a keyboard, a microphone, a pointing and selection device, cameras, video cards, displays, the disk 506, the network devices 520, and so on. The input/output ports 510 may include, for example, serial ports, parallel ports, and USB ports.

The computer 500 can operate in a network environment and thus may be connected to the network devices 520 via the i/o interfaces 518, and/or the i/o ports 510. Through the network devices 520, the computer 500 may interact with a network. Through the network, the computer 500 may be logically connected to remote computers (e.g., mobile devices). Networks with which the computer 500 may interact include, but are not limited to, a LAN, a WAN, and other networks.

In another embodiment, the described methods and/or their equivalents may be implemented with computer executable instructions. Thus, in one embodiment, a non-transitory computer-readable medium is configured with stored computer executable instructions that when executed by a machine (e.g., processor, computer, and so on) cause the machine (and/or associated components) to perform the methods of FIGS. 1 and 2.

While for purposes of simplicity of explanation, the illustrated methodologies in the figures are shown and described as a series of blocks, it is to be appreciated that the methodologies are not limited by the order of the blocks, as some blocks can occur in different orders and/or concurrently with other blocks from that shown and described. Moreover, less than all the illustrated blocks may be used to implement an example methodology. Blocks may be combined or separated into multiple components. Furthermore, additional and/or alternative methodologies can employ additional blocks that are not illustrated.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

ASIC: application specific integrated circuit.
CD: compact disk.
CD-R: CD recordable.
CD-RW: CD rewriteable.
DVD: digital versatile disk and/or digital video disk.
HTTP: hypertext transfer protocol.
LAN: local area network.
PCI: peripheral component interconnect.
PCIE: PCI express.
RAM: random access memory.
DRAM: dynamic RAM.
SRAM: synchronous RAM.
ROM: read only memory.
PROM: programmable ROM.
EPROM: erasable PROM.
USB: universal serial bus.
XML: extensible markup language.
WAN: wide area network.

"Computer component", as used herein, refers to a computer-related entity (e.g., hardware, firmware, instructions in execution, combinations thereof). Computer components may include, for example, a process running on a processor, a processor, an object, an executable, a thread of execution, and a computer. A computer component(s) may reside within a process and/or thread. A computer component may be localized on one computer and/or may be distributed between multiple computers.

"Computer communication", as used herein, refers to a communication between computing devices (e.g., computer, personal digital assistant, cellular telephone) and can be, for example, a network transfer, a file transfer, an applet transfer, an email, an HTTP transfer, and so on. A computer communication can occur across, for example, a wireless system (e.g., IEEE 802.11), an Ethernet system (e.g., IEEE 802.3), a token ring system (e.g., IEEE 802.5), a LAN, a WAN, a point-to-point system, a circuit switching system, a packet switching system, and so on.

"Computer-readable medium", as used herein, refers to a non-transitory medium that stores instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

In some examples, "database" is used to refer to a table. In other examples, "database" may be used to refer to a set of tables. In still other examples, "database" may refer to a set of data stores and methods for accessing and/or manipulating those data stores.

"Logic", as used herein, includes but is not limited to hardware, firmware, a non-transitory computer readable medium that stores instructions, instructions in execution on a machine, and/or combinations of each to perform a function(s) or an action(s), and/or to cause a function or action from another logic, method, and/or system. Logic may include a microprocessor controlled by an algorithm, a discrete logic (e.g., ASIC), an analog circuit, a digital circuit, a programmed logic device, a memory device containing instructions, and so on. Logic may include one or more gates, combinations of gates, or other circuit components. Where multiple logics are described, it may be possible to incorporate the multiple logics into one physical logic. Similarly, where a single logic is described, it may be possible to distribute that single logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, non-transitory computer-readable medium). Logical and/or physical communication channels can be used to create an operable connection.

"User", as used herein, includes but is not limited to one or more persons, computers or other devices, or combinations of these.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the disclosure is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is used in the detailed description or claims (e.g., A or B) it is intended to mean "A or B or both". When the applicants intend to indicate "only A or B but not both" then the phrase "only A or B but not both" will be used. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is used herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be used.

What is claimed is:

1. A non-transitory computer-readable medium storing computer-executable instructions that when executed by a computer cause the computer to:
   receive, from a mobile device via a network communication, a creation request that requests the computer to create a trip report skeleton, where the trip report skeleton is a template that allows trip report data to be inputted and stored on the mobile device;
   identify, by the computer, the creation request and in response, cause an operating system to initiate a first thread and a second thread to separate operations of (i) the creation request and (ii) generating the trip report skeleton, wherein the first thread and the second thread are executed asynchronously;
   assign and process, by the computer to a processor, the creation request in the first thread, wherein the first thread performs:
      in response to the creation request, scheduling a task to generate the trip report skeleton in the second thread; and
      transmitting an electronic acknowledgment acknowledging receipt of the creation request to the mobile device;
   assign and process, by the computer to the processor in the second thread, the task for generating the trip report skeleton, wherein the generating comprises:
      retrieving a canonical trip report including data fields from a database, and combining the canonical trip report with metadata for rendering the data fields from the canonical trip report on a display of a mobile device;
      creating the trip report skeleton in a Self Describing Object (SDO) from the combined canonical trip report and the metadata;
   in response to receiving, by the computer from the mobile device, a fetch request to retrieve the trip report skeleton:
      determining whether the trip report skeleton has been created and:
         when the trip report skeleton is not yet created, canceling the fetch request such that the mobile device is enabled to make a subsequent fetch request for the trip report skeleton;
         when the trip report skeleton has been created, transmitting the trip report skeleton to the mobile device; and
         wherein the metadata allows the mobile device to render the trip report skeleton including the template and the data fields, wherein the trip report skeleton allows the mobile device to input data into the data fields when the mobile device is offline from the computer to minimize network interactions therebetween.

2. The non-transitory computer-readable medium of claim 1, where the instructions further comprise instructions configured to cancel the fetch request after a time out period.

3. The non-transitory computer-readable medium of claim 1, where the instructions further comprise instructions configured to cause the computer to embed the metadata in the trip report skeleton to be used by the mobile device to render the trip report skeleton.

4. The non-transitory computer-readable medium of claim 1, where the trip report skeleton is configured to be populated with trip report data using the mobile device to create a trip report.

5. The non-transitory computer-readable medium of claim 1, where the instructions further comprise sending the trip report to a server side logic by establishing a network link with a server side logic in a clinical research associate (CRA) application framework.

6. The non-transitory computer-readable medium of claim 5, further comprising sending the trip report to a server side logic upon determining that a predetermined percentage of trip report data has been entered in the trip report skeleton.

7. The non-transitory computing computer-readable medium of claim 1, where a trip report skeleton is generated by combining metadata for rendering a trip report skeleton and a canonical trip report.

8. The non-transitory computer-readable medium of claim 1, where data is entered by the mobile device into the skeleton trip report regardless of the accessibility of the data from a server.

9. The non-transitory computer-readable medium of claim 1, where the trip report creation request is sent from the mobile device in a first thread and the trip report skeleton is sent to the mobile device in a second thread.

10. A computing system, comprising:
    a processor operably connected with a non-transitory computer readable medium by a communication bus;

a server side logic stored in the non-transitory computer readable medium and including instructions that when executed by the processor cause the processor to:

receive a request, from a mobile device via a network communication, wherein the request is a creation request that requests the computer to create a trip report skeleton, where the trip report skeleton is a template that allows trip report data to be inputted and stored on the mobile device;

identify, by the computer, that the request is a creation request for a trip report skeleton;

in response to identifying the creation request, cause an operating system to initiate a first thread and a second thread to separate operations of the creation request and generating the trip report skeleton, wherein the first thread and the second thread are executed asynchronously;

assign and process, by the computer to a processor, the creation request in the first thread, wherein the first thread performs:
  in response to the creation request, scheduling creation of the trip report skeleton in the second thread; and
  transmitting an electronic acknowledgment acknowledging receipt of the creation request to the mobile device;

assign and process, by the computer to the processor in the second thread, generating the trip report skeleton, wherein the generating comprises:
  retrieving a canonical trip report including data fields from a database, and combining the canonical trip report with metadata for rendering the data fields from the canonical trip report on a display of a mobile device;
  creating the trip report skeleton in a Self Describing Object (SDO) from the combined canonical trip report and the metadata;

in response to receiving, by the computer from the mobile device, a fetch request to retrieve the trip report skeleton:
  determining whether the trip report skeleton has been created and:
    when the trip report skeleton is not yet created, canceling the fetch request such that the mobile device is enabled to make a subsequent fetch request for the trip report skeleton;
    when the trip report skeleton has been created, transmitting the trip report skeleton to the mobile device; and
  wherein the metadata allows the mobile device to render the trip report skeleton including the template and the data fields, wherein the trip report skeleton allows the mobile device to input data into the data fields when the mobile device is offline from the computer to minimize network interactions therebetween.

11. The computing system of claim 10, further comprising a Self Describing Object (SDO) transformer configured to, in the second thread, combine the canonical trip report and the metadata from the database to generate the trip report skeleton in an SDO format, and wherein the metadata facilitates rendering of the trip report skeleton on a display screen.

12. The computing system of claim 10, where the canonical trip report is generalized so that the canonical trip report can be distributed to different mobile devices.

13. The computing system of claim 10, where the server side logic is further configured to provide application programming interfaces for the mobile device to facilitate loading and synchronizing the trip report skeleton.

14. A method performed by a computer including at least a processor, the method comprising:

receiving, from a mobile device via a network communication, a request;

identifying the request as a creation request that requests the computer to create a trip report skeleton, where the trip report skeleton is a template that allows trip report data to be inputted and stored on the mobile device;

in response to identifying the creation request, initiating, by the computer, a first thread and a second thread to separate operations of the creation request and generating the trip report skeleton, wherein the first thread and the second thread are performed asynchronously;

processing, by the computer, the creation request in the first thread, wherein the first thread performing:
  in response to the creation request, scheduling creation of the trip report skeleton in the second thread; and
  transmitting an acknowledgment acknowledging receipt of the creation request to the mobile device;

in the second thread, generating by the computer, the trip report skeleton, wherein the generating comprises:
  retrieving, from a data storage device, a canonical trip report that includes data fields, and combining the canonical trip report with metadata for rendering the data fields from the canonical trip report on a display of a mobile device;
  creating the trip report skeleton in a Self Describing Object (SDO) from the combined canonical trip report and the metadata;

in response to receiving, by the computer from the mobile device, a fetch request to retrieve the trip report skeleton:
  determining whether the trip report skeleton has been created and:
    when the trip report skeleton is not yet created, allowing the fetch request to time out such that the mobile device is enabled to make a subsequent fetch request for the trip report skeleton; and
    when the trip report skeleton has been created, transmitting the trip report skeleton to the mobile device; and
  wherein the metadata allows the mobile device to render the trip report skeleton including the template and the data fields, wherein the trip report skeleton allows the mobile device to input data into the data fields when the mobile device is offline from the computer to minimize network interactions therebetween.

15. The method of claim 14, further comprising configuring the Self Describing Object of the trip report skeleton to be deserialized on the mobile device into a generic structure that allows the mobile device to display the data fields based on the metadata and allow trip report data to be inputted when the mobile device is not in communication with the computer.

* * * * *

UNITED STATES PATENT AND TRADEMARK OFFICE
CERTIFICATE OF CORRECTION

PATENT NO. : 11,693,882 B2
APPLICATION NO. : 16/810066
DATED : July 4, 2023
INVENTOR(S) : Lynes et al.

It is certified that error appears in the above-identified patent and that said Letters Patent is hereby corrected as shown below:

In the Specification

In Column 2, Line 52, delete "processor" and insert -- processer --, therefor.

Signed and Sealed this
Twenty-eighth Day of May, 2024

Katherine Kelly Vidal
*Director of the United States Patent and Trademark Office*